(12) United States Patent
Hansis et al.

(10) Patent No.: US 10,405,821 B2
(45) Date of Patent: Sep. 10, 2019

(54) IMAGING SYSTEM FOR A VERTEBRAL LEVEL

(71) Applicant: KONINKLIJKE PHILIPS N.V., Eindhoven (NL)

(72) Inventors: Eberhard Sebastian Hansis, Hamburg (DE); Dirk Schaefer, Hamburg (DE); Michael Grass, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/316,215

(22) PCT Filed: Jun. 1, 2015

(86) PCT No.: PCT/EP2015/062150
§ 371 (c)(1),
(2) Date: Dec. 5, 2016

(87) PCT Pub. No.: WO2015/185503
PCT Pub. Date: Dec. 10, 2015

(65) Prior Publication Data
US 2017/0150935 A1 Jun. 1, 2017

(30) Foreign Application Priority Data
Jun. 6, 2014 (EP) .................................... 14171512

(51) Int. Cl.
*A61B 6/00* (2006.01)
*G06T 7/73* (2017.01)
(Continued)

(52) U.S. Cl.
CPC ............ *A61B 6/505* (2013.01); *A61B 5/4566* (2013.01); *A61B 6/4441* (2013.01);
(Continued)

(58) Field of Classification Search
CPC ... A61B 5/4566; A61B 6/4441; A61B 6/4464; A61B 6/505; A61B 6/5241;
(Continued)

(56) References Cited

U.S. PATENT DOCUMENTS 6,850,635 B2  2/2005 Gerard et al.
7,073,939 B2  7/2006 Spahn
(Continued)

FOREIGN PATENT DOCUMENTS

EP  0655861 A1  5/1995
GB  2465771 A   6/2010
(Continued)

*Primary Examiner* — Mekonen T Bekele (57) ABSTRACT

The present invention relates to an imaging system (10) for a vertebral level, an identification method for a vertebral level, a computer program element for controlling such system and a computer readable medium having stored such computer program element. The imaging system (10) comprises a determination unit (11), a definition unit (12), an imaging unit (13), and a processing unit (14). The determination unit (11) determines a target vertebral level. The definition unit (12) defines an anatomical landmark of a spine. The imaging unit (13) provides a series of X-ray images along the spine based on the landmark. The processing unit (14) identifies the target vertebral level in at least one of the X-ray images. The processing unit (14) further stitches the X-ray images to a continuous panoramic image of the spine and identifies the target vertebral level in the panoramic image.

13 Claims, 4 Drawing Sheets

(51) Int. Cl.
  *A61B 5/00* (2006.01)
  *G06T 11/60* (2006.01)
(52) U.S. Cl.
  CPC .......... *A61B 6/4464* (2013.01); *A61B 6/5241* (2013.01); *A61B 6/5276* (2013.01); *A61B 6/547* (2013.01); *G06T 7/73* (2017.01); *G06T 11/60* (2013.01); *G06T 2207/10116* (2013.01); *G06T 2207/30012* (2013.01)
(58) Field of Classification Search
  CPC ....... A61B 6/5276; A61B 6/547; G06T 11/60; G06T 7/73; G06T 2207/10116; G06T 2207/30012
  See application file for complete search history.

(56) References Cited

U.S. PATENT DOCUMENTS

| | | | |
|---|---|---|---|
| 7,095,881 | B2 | 8/2006 | Lelong et al. |
| 7,555,100 | B2 | 6/2009 | Wang et al. |
| 7,831,096 | B2 | 11/2010 | Wiliamson |
| 8,509,502 | B2 * | 8/2013 | Porat .......... G06T 7/11 382/128 |
| 9,320,569 | B2 | 4/2016 | Lloyd et al. |
| 9,795,414 | B2 * | 10/2017 | Ledet .......... A61B 17/7029 |
| 10,251,594 | B2 * | 4/2019 | Klinder .......... A61B 6/466 |
| 2008/0132949 | A1 * | 6/2008 | Aferzon .......... A61F 2/446 606/246 |
| 2008/0152088 | A1 | 6/2008 | Wang et al. |
| 2009/0091567 | A1 * | 4/2009 | Fu .......... A61B 6/5235 345/419 |
| 2010/0280550 | A1 * | 11/2010 | Reo .......... A61B 17/7062 606/249 |
| 2011/0058720 | A1 * | 3/2011 | Lu .......... G06T 7/344 382/131 |
| 2011/0276179 | A1 | 11/2011 | Banks |
| 2012/0172700 | A1 | 7/2012 | Krishnan |
| 2012/0289826 | A1 | 11/2012 | Graumann |
| 2014/0257395 | A1 * | 9/2014 | Ledet .......... A61B 17/7007 606/257 |
| 2017/0245895 | A1 * | 8/2017 | Ledet .......... A61B 17/7026 |
| 2017/0367645 | A1 * | 12/2017 | Klinder .......... A61B 6/466 |

FOREIGN PATENT DOCUMENTS

| | | |
|---|---|---|
| JP | 2004275361 A | 10/2004 |
| JP | 2006136724 A | 6/2006 |
| JP | 2009090022 A | 4/2009 |
| JP | 2012045313 A | 3/2012 |
| WO | 200228284 A1 | 4/2002 |
| WO | 2005088520 A1 | 9/2005 |
| WO | 2012119856 A1 | 9/2012 |
| WO | 2013132235 A1 | 9/2013 |

\* cited by examiner

IMAGING SYSTEM FOR A VERTEBRAL LEVEL

CROSS-REFERENCE TO PRIOR APPLICATIONS

This application is the U.S. National Phase application under 35 U.S.C. § 371 of International Application No. PCT/EP2015/062150, filed on Jun. 1, 2015, which claims the benefit of European Patent Application No. 14171512.8, filed on Jun. 6, 2014. These applications are hereby incorporated by reference herein.

FIELD OF THE INVENTION

The present invention relates to an imaging system for a vertebral level, an identification method for a vertebral level, a computer program element for controlling such system and a computer readable medium having stored such computer program element.

BACKGROUND OF THE INVENTION

In minimally invasive spine interventions, it is very important to localize the correct vertebral level for treatment. The interventions are usually performed under X-ray guidance, with the X-ray system offering only a limited field-of-view. However, only few vertebral levels can reliably be identified from their shape or the surrounding anatomy in such assembled image. Therefore, the vertebral level has to be identified by palpation and counting of landmarks or from visually assessing projection images from the limited X-ray field-of-view. As a result, the process is complicated and error-prone.

In digital X-ray imaging, a composition of an image from sub-images is generally used to form a composite image of an elongate scene which is too long to be reproduced in one operation. Using a contemporary digital X-ray examination apparatus, it is difficult or even impossible to form an X-ray image of the complete region of the spinal column of the patient to be examined in one exposure. A number of successive X-ray images of portions of the region to be examined are formed, which images together cover the entire region. A method of this kind is also called the translation reconstruction technique and is known from EP 0 655 861 A1.

Further, US2011/0276179 A1 discloses designating beginning and end points of a desired AP radiograph. A robotic system can retrace this path obtaining a contiguous X-ray image. The entire scan can be displayed on a computer screen. A surgeon can designate one or more desired surgical levels in the displayed scan. A further robotic system may hold a marker in place over the designated vertebral body while a confirmatory radiograph is obtained.

SUMMARY OF THE INVENTION

Hence, there may be a need to provide an imaging system for a vertebral level, which enables an easier and more reliable identification of the target vertebral level in an interventional setting.

The problem of the present invention is solved by the subject-matters of the independent claims, wherein further embodiments are incorporated in the dependent claims. It should be noted that the aspects of the invention described in the following apply also to the imaging system for identification of a vertebral level, the identification method for a vertebral level, the computer program element, and the computer readable medium.

According to the present invention, an imaging system for a vertebral level is presented. The imaging system comprises a determination unit, a definition unit, an imaging unit, and a processing unit. The determination unit is configured to receive pre-interventional image data and determine a target vertebral level using this pre-interventional image data. The determination may be made automatically. The determination unit may be an interface to an input device, so that the input regarding the target vertebra level may be provided manually by a user.

The imaging unit is configured to provide a series of X-ray images along the spine based on a landmark. The landmark may be a characteristic of a 1st thoracic vertebrae, a 12th thoracic vertebrae, a 1st cervical vertebrae, a 2nd cervical vertebrae, a 7th cervical vertebrae, a sacrum and/or the like. The term "based on" means that the series of X-ray images is taken based on one of more landmarks. Thereby, the landmark can be a start, end or center point for the images, a particular point of interest, and/or the images can be taken along a series of at least two landmarks and the like. The X-ray images can be stitched together to form a panoramic image of the spine.

The definition unit is configured to define an anatomical landmark of a spine. The definition of a landmark can be done by registration of the pre-interventional data (CT, MR or else) to a panoramic image and/or by registration of a patient-specific or general model to the panoramic image. The processing unit is configured to identify the target vertebral level in at least one of the X-ray images based on the determination in the pre-interventional image data.

In other words, a target vertebral level or disk space is determined. The target vertebral level or disk space is e.g. known by name (e.g., L2—second lumbar vertebra) or it can be known from pre-interventional CT or MRI data or else.

A reliably identifiable anatomical landmark of a spine is defined, which indicates preferably a characteristic as e.g. a center, uppermost or lowest point of a 1st thoracic vertebrae, a 12th thoracic vertebrae, a 1st cervical vertebrae, a 2nd cervical vertebrae, a 7th cervical vertebrae, a sacrum and/or the like.

Based on or starting from the landmark, a series of X-ray images or frames is provided or preferably acquired while moving a patient table or an imaging system in-between the frames e.g. towards a region near the target vertebral level or starting from a region near the target vertebral level. A limited overlap between the frames is preferred.

The target vertebral level is then identified in at least one of the X-ray images. Having a reliably identifiable landmark in the same (panoramic) image as the target vertebral level, this identification can be done based on a pre-interventional data set with marked target position, whereby an identification of the target vertebral level can be done automatically through registration of the pre-interventional data set or of a projective view of the pre-interventional data to the series of X-ray images along the spine or to the panoramic image. Such registration may advantageously include or rely on registration of the defined anatomical landmark, which provides a registration having a relatively high level of accuracy.

Once the target vertebral level is identified in a e.g. current or last X-ray image, which means it is within the field of view of the imaging device, it can be marked either physically e.g. by placing a position marker on the patient skin and/or electronically e.g. by storage of current x-ray system and patient table positions. At this point, the X-ray image acquisition may either be stopped to keep the X-ray dose received by the patient to a minimum, or it may continue in order to obtain a more complete panoramic image covering a larger region of the spine.

As the imaging system for a vertebral level according to the invention is based on a series of images and as the series of images is based on a defined anatomical landmark of the spine, the device according to the invention enables a very easy and reliable identification of the target vertebral level in an interventional setting. In particular, a risk of mis-identifying the treated vertebral level is greatly reduced.

Further, the dose of the acquisition can be chosen very low, as the spine X-ray images are not used for direct diagnostic use. Furthermore, the device according to the invention can be implemented on existing imaging systems even without availability of C-arm motion tracking or table motion tracking.

In an example, the determination unit is further or additionally configured to indicate the target vertebral level in the pre-interventional image data.

In an example, the determination unit is further or additionally configured to extract the spine in the pre-interventional image data by segmentation and in particular by model-based segmentation using a model of the spine. The output of the segmentation is then a patient-specific spine model.

In an example, the determination unit is further or additionally configured to provide a general spine model, to determine the target vertebral level based on the general spine model and to indicate the target vertebral level in the general spine model. The imaging system may further comprise a registration unit configured to register the general spine model with at least one X-ray image and/or a panoramic image (explained below) and to indicate the target vertebral level in the at least one X-ray image and/or the panoramic image based on the indication in the general spine model.

In an example, the processing unit is further configured to stitch the X-ray images or frames to a preferably continuous panoramic image of the spine and to identify the target vertebral level in the panoramic image. An overlap between the frames is required for a continuous panoramic image. The stitching can be based on e.g. the image content and/or external markers attached to the patient and/or the table. The stitched panoramic image offers a preferably continuous view from the known and identified landmark up to the current imaging position, which makes an identification of the target vertebral level in the current image easy and safe.

If a pre-interventional data set (CT, MR or else) with marked target position is available, an identification of the target vertebral level can be done automatically through registration of the pre-interventional data set or of a projective view of the pre-interventional data to the series of X-ray images along the spine or to the panoramic image.

Additionally, model-based segmentation methods may be used to extract the spinal column in the pre-interventional data and to register it to the panorama image. Even without a patient-specific model, a general model of the spinal column can be registered to the panoramic image to facilitate vertebral level identification.

Once a target vertebral level has been identified and is in the field-of-view of the X-ray system, it can be marked on the patient's skin or recorded electronically from tracked positions of the patient table and imaging system.

In an example, the imaging system for a vertebral level further comprises an input device configured to enable the determination of the target vertebral level. The input device may be instead or additionally configured to enable the identification of the target vertebral level in the at least one X-ray image and/or in the panoramic image.

In an example, the imaging system for a vertebral level further comprises a motion unit configured to provide a motion signal for moving a patient table and/or the imaging unit.

The imaging system may further comprise a tracking unit configured to provide a tracking signal for tracking the motion of the patient table and/or of the imaging unit. The tracking unit may be at least one sensor positioned at the patient table and/or the imaging unit. The sensor may be a position sensor and/or an acceleration sensor or the like.

If a tracking of the table or the X-ray system motion is available, the device can give guidance to a user at which position to acquire the next frame for stitching to minimize dose while retaining sufficient coverage.

In an example, the imaging system for a vertebral level further comprises a recording unit configured to record the position of the target vertebral level based on the tracked position of the patient table and/or of the imaging unit.

The imaging system may further comprise a marking unit configured to mark the target vertebral level on the patient's skin.

In an example, the imaging system for a vertebral level further comprises a registration unit configured to register the pre-interventional image data with the at least one X-ray image and/or the panoramic image. The registration unit may be further configured to indicate the target vertebral level in the at least one X-ray image and/or in the panoramic image based on the indication in the pre-interventional image data.

The imaging system may further comprise an X-ray acquisition device for acquiring a series of X-ray images and a display unit. The system may further comprise a patient table.

According to the present invention, also an identification method for a vertebral level is presented. It comprises the following steps, not necessarily in this order:
a) determining a target vertebral level,
b) defining an anatomical landmark of a spine,
c) providing a series of X-ray images along the spine based on the landmark, and
d) identifying the target vertebral level in at least one of the X-ray images.

The definition of a landmark can be done by registration of pre-interventional data to a panoramic image and/or by registration of a patient-specific or general model to the panoramic image.

The identification can be done by a 'counting' method, manually or automatically. Alternatively, if a pre-interventional data set (CT, MR or else) with marked target position is available, an identification of the target vertebral level can be done automatically through registration of the pre-interventional data set or of a projective view of the pre-interventional data to the series of X-ray images along the spine or to the panoramic image.

Of course, both approaches can be combined to use a single, reliably identifiable landmark to guide the registration of the pre-interventional image data or of the model.

According to the present invention, also a computer program for controlling an imaging system for a vertebral level is presented, wherein the computer program comprises program code means for causing an imaging system as defined in the independent device claim to carry out the steps of the identification method for a vertebral level as defined in the independent method claim, when the computer program is run on a computer controlling the imaging system.

It shall be understood that the imaging system for a vertebral level, the identification method for a vertebral level, the computer program element for controlling such system and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
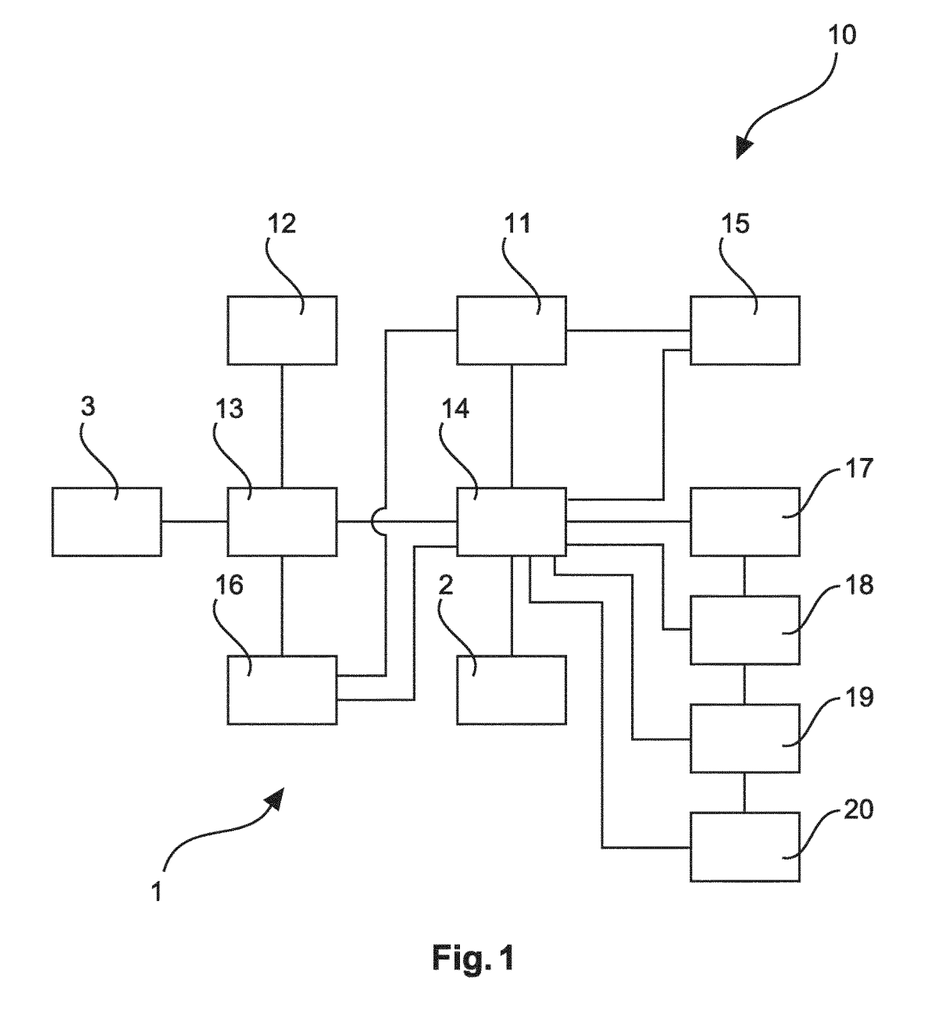
FIG. 1 shows a schematic drawing of an example of an imaging system for a vertebral level.

FIG. 1 shows schematically and exemplarily an embodiment of an imaging system 1 an X-ray acquisition device 3 for acquiring a series of X-ray images and a display unit 2 for displaying images. The system further comprises a patient table (not shown).

The imaging system 10 comprises a determination unit 11, a definition unit 12, an imaging unit 13 and a processing unit 14.

The determination unit 11 determines a target vertebral level. The determination may be made automatically. The determination unit may be an interface to an input device 15, so that the determination may be made manually by a user.

The definition unit 12 defines an anatomical landmark of a spine and is connected with the imaging unit 13. The imaging unit 13 provides a series of X-ray images along the spine based on the landmark. For receiving X-ray image data, the imaging unit 13 is connected with the X-ray acquisition device 3. Thus, the imaging unit 13 provides images based on X-ray image data from the X-ray acquisition device 3, the image data being acquired e.g. starting at a landmark and/or along a series of at least two landmarks. The processing unit 14 identifies the target vertebral level in at least one of the X-ray images. The processing unit 14 further stitches the X-ray images to a continuous panoramic image of the spine and identifies the target vertebral level in the panoramic image. The stitching can be based on e.g. the image content and/or external markers attached to the patient and/or the table. The processing unit 14 may be connected with the determination unit 11 and the display unit 2 for displaying one of more of the X-ray images and/or the panoramic image of the spine.

The imaging system 10 further comprises an input device 15 to enable the determination of the target vertebral level and to enable the identification of the target vertebral level in the X-ray image and/or in the panoramic image. The determination may be made manually by a user and/or automatically be the device. The input device 15 may be connected with the determination unit 11 and the processing unit 14.

The imaging system 10 further comprises a motion unit 17 connected with the processing unit 14 to provide a motion signal for moving a patient table and/or the imaging unit 13. The imaging system 10 further comprises a tracking unit 18 connected with the processing unit 14 to provide a tracking signal for tracking the motion of the patient table and/or of the imaging unit 13. The tracking unit 18 may be also connected with the motion unit 17 and/or the table (not shown).

The imaging system 10 further comprises a recording unit 19 connected with the processing unit 14 to record the position of the target vertebral level based on the tracked position of the patient table and/or of the imaging unit 13. The recording unit 19 may be also connected with the tracking unit 18 and/or the imaging unit 13 (connection not shown).

The imaging system 10 further comprises a marking unit 20 connected with the processing unit 14 to mark the target vertebral level on the patient's skin.

The imaging system 10 further comprises a registration unit 16 to register pre-interventional image data with the X-ray image and/or the panoramic image. Based on this registration, the target vertebral level may be indicated in the X-ray image and/or in the panoramic image based on the in accordance with the determined target vertebral level in the pre-interventional image data. The registration unit 16 may be connected with the imaging unit 13, the determination unit 11 and the processing unit 14.

Instead or additionally, also model-based segmentation methods may be used to extract the spinal column in the pre-interventional data and to register it to the panoramic image. Even without a patient-specific model, a general model of the spinal column can be registered to the panoramic image to facilitate vertebral level identification.

Once a target vertebral level has been identified and is in the field-of-view of the X-ray system, it can be marked on the patient's skin, or tracked positions of the patient table and imaging system can be recorded electronically.

Figure 2:
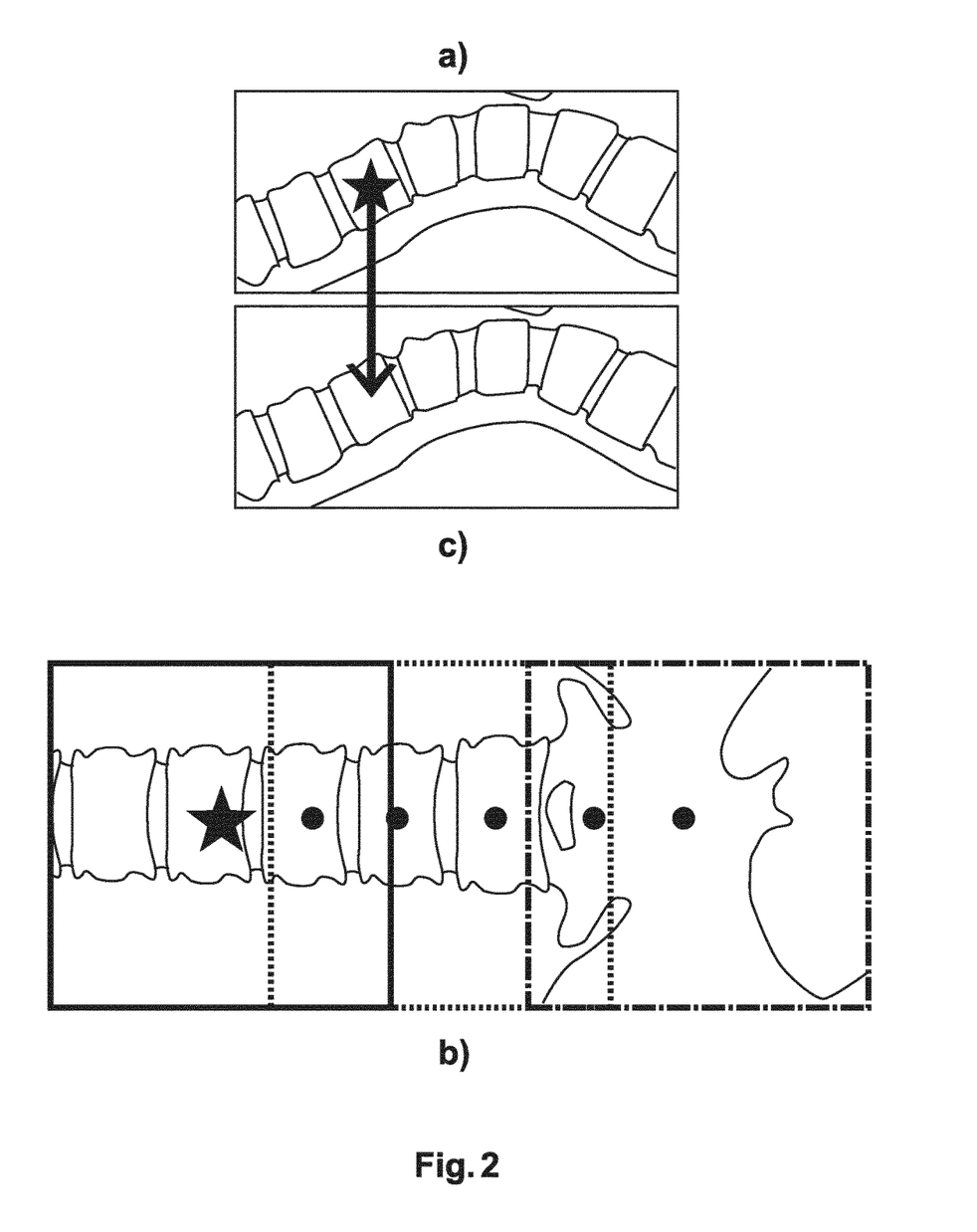
FIG. 2a shows a pre-operative image of a spine.
FIG. 2b shows a panoramic image stitched from several single images of a series of X-ray images along the spine.
FIG. 2c shows another panoramic image of the spine.

FIG. 2a shows a pre-operative MRI (magnetic resonance imaging) or CT (computed tomography) image of a spine. The pre-interventional image data is provided to determination unit 11, which uses this data to determine the target vertebral level. The target vertebral level is, for illustrative purposes only, indicated in the drawing by a star-shaped marker. The determination may be made based on user input on an input device, so that the target vertebral level may be provided manually by a user. The target vertebral level may also be determined automatically, for example, based on a diagnosis or treatment indication stored in an electronic patient record or otherwise.

FIG. 2b shows a panoramic image stitched from several single images of a series of X-ray images along the spine. The single images or separate frames are shown by differently broken boxes. The image is based on a reliably identifiable anatomical landmark, the sacrum. The five round markers symbolize 'counting' i.e. intermediate vertebrae between the sacrum and the target vertebral level.

The pre-operative image is registered to the panoramic image. As shown by the arrow between FIG. 2a and FIG. 2c (another panoramic image of the spine), the registration allows for the position of the target vertebral level to be accurately inferred from the pre-operative image to the panoramic image. Once the target vertebral level is identified in the X-ray image or panoramic image, i.e. the X-ray imaging system has been positioned so that the target vertebra is within its field-of-view, the target vertebral level may be indicated with a star-shaped marker or any other suitable marker.

Figure 3:
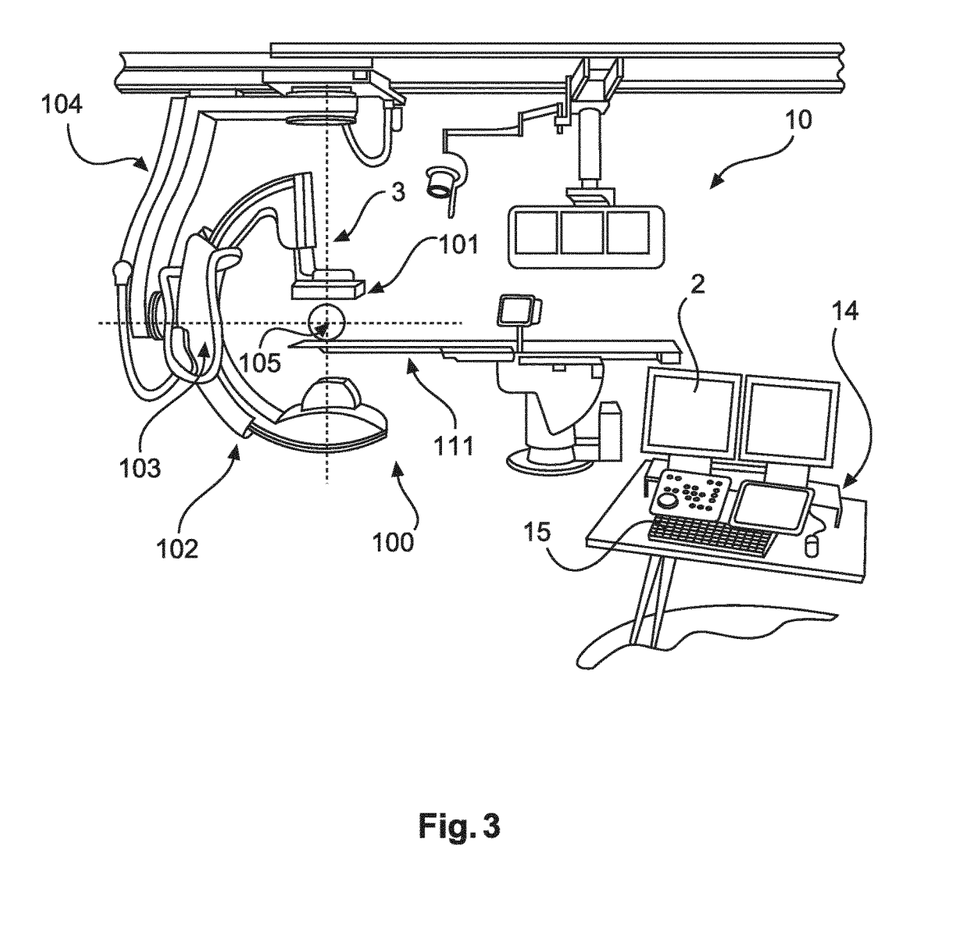
FIG. 3 shows a further schematic drawing of another example of an imaging system for a vertebral level.

FIG. 3 shows schematically an X-ray imaging system 10. It comprises the X-ray image acquisition device 3 with a source of X-ray radiation 100 provided to generate X-ray radiation. The X-ray acquisition device 3 acquires a series of X-ray images to be provided by the imaging unit 13 (not shown). A table 111 is provided to receive a subject to be examined. An X-ray image detection module 101 is located opposite the source of X-ray radiation 100, i.e. during the radiation procedure, the subject is located between the source of X-ray radiation 100 and the detection module 101.

Figure 4:
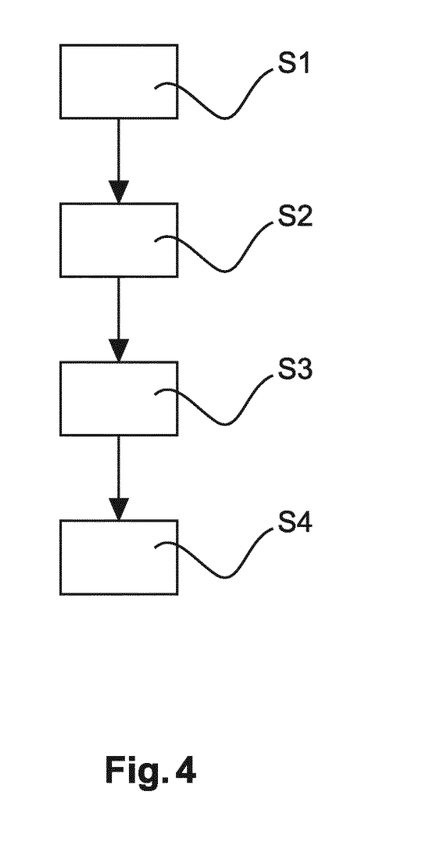
FIG. 4 shows a schematic overview of steps of an identification method for a vertebral level.

The X-ray source 100 and a detector 101 are mounted to the ends of a C-arm 102. The C-arm 102 is held by curved rail, the "sleeve" 103. The C-arm can slide in the sleeve 103, thereby performing a "roll movement" about the axis of the C-arm. The sleeve 103 is attached to an L-arm 104 via a rotational joint and can perform a "propeller movement" about the axis of this joint. The L-arm 104 is attached to the ceiling via another rotational joint and can perform a rotation about the axis of this joint. The various rotational movements are effected by servo motors. The axes of the three rotational movements and the cone-beam axis always meet in a single fixed point, the "isocenter" 105 of the rotational X-ray scanner. The various rotational movements are controlled by a control unit 112. Each triple of C-arm angle, sleeve angle, and L-arm angle defines a position of the X-ray source 100. By varying these angles with time, the source 100 can be made to move along a prescribed source trajectory. The detector 101 at the other end of the C-arm 102 makes a corresponding movement. The source trajectory will be confined to the surface of an isocentric sphere. It is noted that the example shown is of a so-called C-type X-ray imaging system 10. Of course, the invention also relates to other types of imaging systems 10. The processing unit 14 identifies the target vertebral level in at least one of the X-ray images provided by the imaging unit 13 (not shown) and acquired by the X-ray acquisition device 3. The processing unit 14 further stitches the X-ray images to a continuous panoramic image of the spine and identifies the target vertebral level in the panoramic image. The processing unit 14 is connected with the determination unit 11 (not shown) and the display unit 2 for displaying one of more of the X-ray images and/or the panoramic image of the spine. The display unit 2 is arranged in the vicinity of the table 111 to display information to the person operating the X-ray imaging system, i.e. a clinician. The input device 15 is arranged to input information by the user, as to determine a target vertebral level. FIG. 4 shows a schematic overview of steps of an identification method for a vertebral level. The method comprises the following steps, not necessarily in this order:

In a first step S1, a target vertebral level is determined.

In a second step S2, an anatomical landmark of a spine is defined.

In a third step S3, a series of X-ray images along the spine based on the landmark is provided.

In a fourth step S4, the target vertebral level is identified in at least one of the X-ray images.

With pre-interventional data being used, the definition of a single landmark in step S2 and the identification of the target vertebral level in step S4 can be done by registration of the pre-interventional data to the panoramic image. Also with a patient-specific or a general model being used, the definition of a single landmark in step S2 and the identification of the target vertebral level in step S4 can be done by registration of the model to the panoramic image. Of course, both approaches can be combined to use a single, reliably identifiable landmark to guide the registration of the pre-interventional image data or of the model.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An imaging system for a vertebral level comprising:
   a determination unit configured to receive pre-interventional image data and to determine a target vertebral level using pre-interventional image data;
   a definition unit configured to define an anatomical landmark of a spine;
   an X-ray acquisition device configured to acquires a series of X-ray images;
   an imaging unit configured to provide the series of X-ray images along the spine based on the anatomical landmark; and
   a processing unit configured to identify the target vertebral level in at least one of the series of X-ray images based on the determination using the pre-interventional image data.

2. Imaging system according to claim 1, wherein the processing unit is further configured to stitch the series X-ray images to a panoramic image of the spine and to identify the target vertebral level in the panoramic image.

3. Imaging system according to claim 1, further comprising an input device configured to enable the determination of the target vertebral level and/or to enable identification of the target vertebral level in the at least one of the series X-ray images.

4. Imaging system according to claim 1, wherein the determination unit is further configured to indicate the target vertebral level in the pre-interventional image data.

5. Imaging system according to claim 1, further comprising a registration unit configured to register the pre-interventional image data with the at least one X-ray image and/or the panoramic image.

6. Imaging system according to claim 4, wherein the determination unit is configured to extract the spine in the pre-interventional image data by segmentation.

7. Imaging system according to claim 6, wherein the determination unit is further configured to receive a general spine model for use in the segmentation.

8. Imaging system according to claim 1, wherein the anatomical landmark indicates preferably a characteristic of at least one of the group of $1^{st}$ thoracic vertebrae, $12^{th}$ thoracic vertebrae, $1^{st}$ cervical vertebrae, $2^{nd}$ cervical vertebrae, $7^{th}$ cervical vertebrae and/or sacrum.

9. Imaging system according to claim 8, further comprising a motion unit configured to provide a motion signal for moving a patient table and/or the imaging unit, and preferably a tracking unit configured to provide a tracking signal for tracking the motion of the patient table and/or of the imaging unit.

10. Imaging system according to claim 9, further comprising a recording unit configured to record a position of the target vertebral level based on a tracked position of the patient table and/or of the imaging unit, and/or further comprising a marking unit configured to mark the target vertebral level on a patient's skin.

11. An identification method for a vertebral level comprising the following steps:
    determining a target vertebral level in pre-interventional image data,
    defining an anatomical landmark of a spine,
    providing a series of X-ray images along the spine based on the anatomical landmark, and
    identifying the target vertebral level in at least one of the X-ray images based on the determination in the pre-interventional image data.

12. A non-transitory computer readable medium, having stored thereon a computer program, executable by a computing unit for controlling a system according to claim 1, which, when being executed by the computing unit, is adapted to perform the identification method of determining a target vertebral level in pre-interventional image data.

13. A computer readable medium having stored the computer program element of the claim 11.

* * * * *